United States Patent
Jolly

(10) Patent No.: US 8,718,785 B2
(45) Date of Patent: May 6, 2014

(54) COCHLEAR TISSUE PROTECTION FROM ELECTRODE TRAUMA

(75) Inventor: Claude Jolly, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 781 days.

(21) Appl. No.: 12/574,760

(22) Filed: Oct. 7, 2009

(65) Prior Publication Data

US 2010/0087905 A1    Apr. 8, 2010

Related U.S. Application Data

(60) Provisional application No. 61/103,732, filed on Oct. 8, 2008.

(51) Int. Cl.
    *A61N 1/18*    (2006.01)
    *A61N 1/36*    (2006.01)

(52) U.S. Cl.
    CPC ................................. *A61N 1/36032* (2013.01)
    USPC .......................................................... 607/55

(58) Field of Classification Search
    CPC . A61N 1/36032; A61N 1/0541; H04R 25/60; H04R 25/65; H04R 25/606; H04R 25/608
    USPC ........ 181/129, 130; 381/328; 607/55–57, 137
    See application file for complete search history.

(56) References Cited

U.S. PATENT DOCUMENTS

| | | | |
|---|---|---|---|
| 5,077,352 A | 12/1991 | Elton | 525/409 |
| 5,458,631 A | 10/1995 | Xavier | 607/117 |
| 5,476,446 A | 12/1995 | Arenburg | 604/21 |
| 5,545,219 A * | 8/1996 | Kuzma | 623/10 |
| 5,645,062 A | 7/1997 | Anderson | 600/391 |
| 5,667,514 A | 9/1997 | Heller | 606/108 |
| 5,676,655 A | 10/1997 | Howard, III et al. | 604/116 |
| 5,713,847 A | 2/1998 | Howard, III et al. | 604/21 |
| 6,078,841 A | 6/2000 | Kuzma | 607/137 |
| 6,127,597 A * | 10/2000 | Beyar et al. | 606/86 R |
| 6,129,685 A | 10/2000 | Howard, III | 600/585 |
| 6,149,657 A | 11/2000 | Kuzma | 606/129 |
| 6,156,728 A | 12/2000 | Gao | 514/12 |

(Continued)

FOREIGN PATENT DOCUMENTS

| | | | |
|---|---|---|---|
| EP | 0633031 A1 | 1/1995 | A61L 27/00 |
| WO | WO 99/22806 | 5/1999 | |

OTHER PUBLICATIONS

Mynatt, Robert, et al, "Demonstration of a Longitudinal Concentration Gradient Along Scala Tympani by Sequential Sampling of Perilymph from the Cochlear Apex", *Journal of the Association for Research in Otolaryngology*, JARO 7: (2006), pp. 182-193.

(Continued)

*Primary Examiner* — Christopher D Koharski
*Assistant Examiner* — Frances Oropeza
(74) *Attorney, Agent, or Firm* — Sunstein Kann Murphy & Timbers LLP

(57) ABSTRACT

A cochlear implant device includes an electrode shell for insertion into a fixed position in cochlear tissue. The electrode shell includes an interior volume that partially encases an implant electrode so that its electrode contacts are exposed for delivering electrical stimulation signals to the cochlear tissue. The electrode shell allows insertion and removal of the implant electrode with minimal trauma to the cochlear tissue.

10 Claims, 3 Drawing Sheets

(56) References Cited

U.S. PATENT DOCUMENTS

| | | | | |
|---|---|---|---|---|
| 6,163,729 | A | 12/2000 | Kuzma | 607/137 |
| 6,195,586 | B1 | 2/2001 | Kuzma | 607/137 |
| 6,263,225 | B1 | 7/2001 | Howard, III | 600/378 |
| 6,304,787 | B1 | 10/2001 | Kuzma et al. | 607/137 |
| 6,309,410 | B1 | 10/2001 | Kuzma et al. | 607/137 |
| 6,377,849 | B1 | 4/2002 | Lenarz et al. | 604/21 |
| 6,440,102 | B1 | 8/2002 | Arenberg et al. | 604/96.01 |
| 7,044,942 | B2 | 5/2006 | Jolly et al. | 604/891.1 |
| 7,240,416 | B2 | 7/2007 | Milojevic et al. | 29/592.1 |
| 2004/0078057 | A1 | 4/2004 | Gibson | 607/3 |
| 2006/0039946 | A1 | 2/2006 | Heruth et al. | 424/422 |
| 2006/0184143 | A1* | 8/2006 | Jolly et al. | 604/288.02 |
| 2007/0026041 | A1 | 2/2007 | Desnoyer et al. | 424/426 |
| 2007/0088335 | A1 | 4/2007 | Jolly | 604/891.1 |
| 2007/0225776 | A1* | 9/2007 | Fritsch et al. | 607/57 |
| 2008/0071269 | A1* | 3/2008 | Hilario et al. | 606/50 |
| 2009/0143848 | A1* | 6/2009 | Greenberg et al. | 607/137 |

OTHER PUBLICATIONS

European Patent & Trademark Office, International Search Report and Written Opinion, PCT/US2008/065253, dated Sep. 3, 2008.
European Patent Office, International Search Report, PCT/US2009/059767, Jan. 15, 2010.

* cited by examiner

COCHLEAR TISSUE PROTECTION FROM ELECTRODE TRAUMA

This application claims priority from U.S. Provisional Patent Application 61/103,732, filed Oct. 8, 2009, which is incorporated herein by reference.

FIELD OF THE INVENTION

The present invention relates to medical implants, and more specifically to cochlear implant systems.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by a cochlear implant that electrically stimulates auditory nerve tissue with small currents delivered by multiple electrode contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission by an external coil 107 into an implant receiver 108. Besides extracting the audio information, the implant receiver 108 may perform additional signal processing such as error correction, pulse formation, etc., and produces a stimulation pattern (based on the extracted audio information) that is sent through connected wires 109 to an implant electrode 110. Typically, the implant electrode 110 includes multiple electrodes on its surface that provide selective stimulation of the cochlea 104.

Insertion and placement and insertion of the implant electrode 110 into the cochlea 104 causes trauma to the cochlear tissue due to the rigidity, friction, and impact of moving the implant electrode 110 through the cochlea 104. For example, insertion of the implant electrode 110 may damage soft tissues, membranes, thin bony shelves, blood vessels, neural elements, etc. In the case of multiple insertions, the damage can accumulate. In addition, removal and replacement of the implant electrode 110 due to device failure or aging is also a serious problem. For example, patients with some residual hearing now receive hybrid implant systems that also include acoustic-mechanical stimulation components, and further hearing loss could occur when the implant electrode 110 is removed or replaced. In addition, there are efforts to use therapeutic drugs to regrow neural tissue around an inserted implant electrode 110 which could suffer catastrophic consequences when the electrode is removed since any new neural tissue growth that might reach the electrode could be disrupted or destroyed.

Thus, designers of the implant electrode 110 work hard to ensure that it is soft and flexible to minimize the insertion trauma. The implant electrode 110 also is constrained to have a uniform external aspect with a smooth outer surface. The impact of electrode insertion in certain regions of the inner ear is also addressed by using a pre-shaped (i.e., pre-curved) implant electrode 110. But the issues associated with cummulative permanent trauma due to multiple explantation and re-implantion of the implant electrode 110 has not been addressed.

SUMMARY OF THE INVENTION

Embodiments of the present invention are directed to a cochlear implant electrode shell for insertion into a fixed position in cochlear tissue. The electrode shell includes an interior volume that partially encases an implant electrode so that its electrode contacts are exposed for delivering electrical stimulation signals to the cochlear tissue.

The electrode shell may also include an electrode release connection for releasing the implant electrode from the electrode shell for retracting the implant electrode with minimal trauma to the cochlear tissue. In addition or alternatively, the electrode shell may include an electrode capture connection for capturing the implant electrode within the electrode shell for inserting the implant electrode with minimal trauma to the cochlear tissue.

In further specific embodiments, the electrode shell may include a therapeutic substance for release into the cochlear tissue, for example, as a coating on the outer surface of the electrode shell or as a substance that is integrated into the body of the electrode shell. There may also be a lubricant coating on the outer surface of the electrode shell to reduce friction for insertion in the cochlear tissue.

The electrode shell may also provide electrical isolation of the electrode contacts from cochlear tissue around the electrode shell. The electrode shell may also directionally shape the electrical stimulation signals to direct them to specific target sites.

The electrode shell may be made of a polymer substance. The electrode shell may be pre-curved for proper fit in the fixed position. The electrode shell also may be adapted to initially be flexible for insertion into the fixed position, and then to harden to become non-flexible after insertion into the fixed position.

Embodiments of the present invention also include a cochlear implant electrode covered by an electrode shell according to any of the above.

DETAILED DESCRIPTION OF SPECIFIC EMBODIMENTS

Embodiments of the present invention are directed to a tissue protector that protects surrounding cochlear tissue from electrode insertion and removal trauma. An electrode shell is provided for insertion into a fixed position in cochlear tissue. The interior volume of the electrode shell partially encases the implant electrode so that its electrode contacts are exposed for delivering electrical stimulation signals to audio neural tissue in the cochlea. The electrode shell allows insertion and removal of the implant electrode with minimal trauma to the cochlear tissue. For example, a penetrating electrode can be implanted into a target location such as into or near the inferior colliculus, the cortex, cochlear nucleus, or auditory nerve, and electrode extraction and re-implantation is facilitated by preserving neural tissue close to the implant electrode, using a electrode shell which stays permanently in place in the body location.

Figure 1:
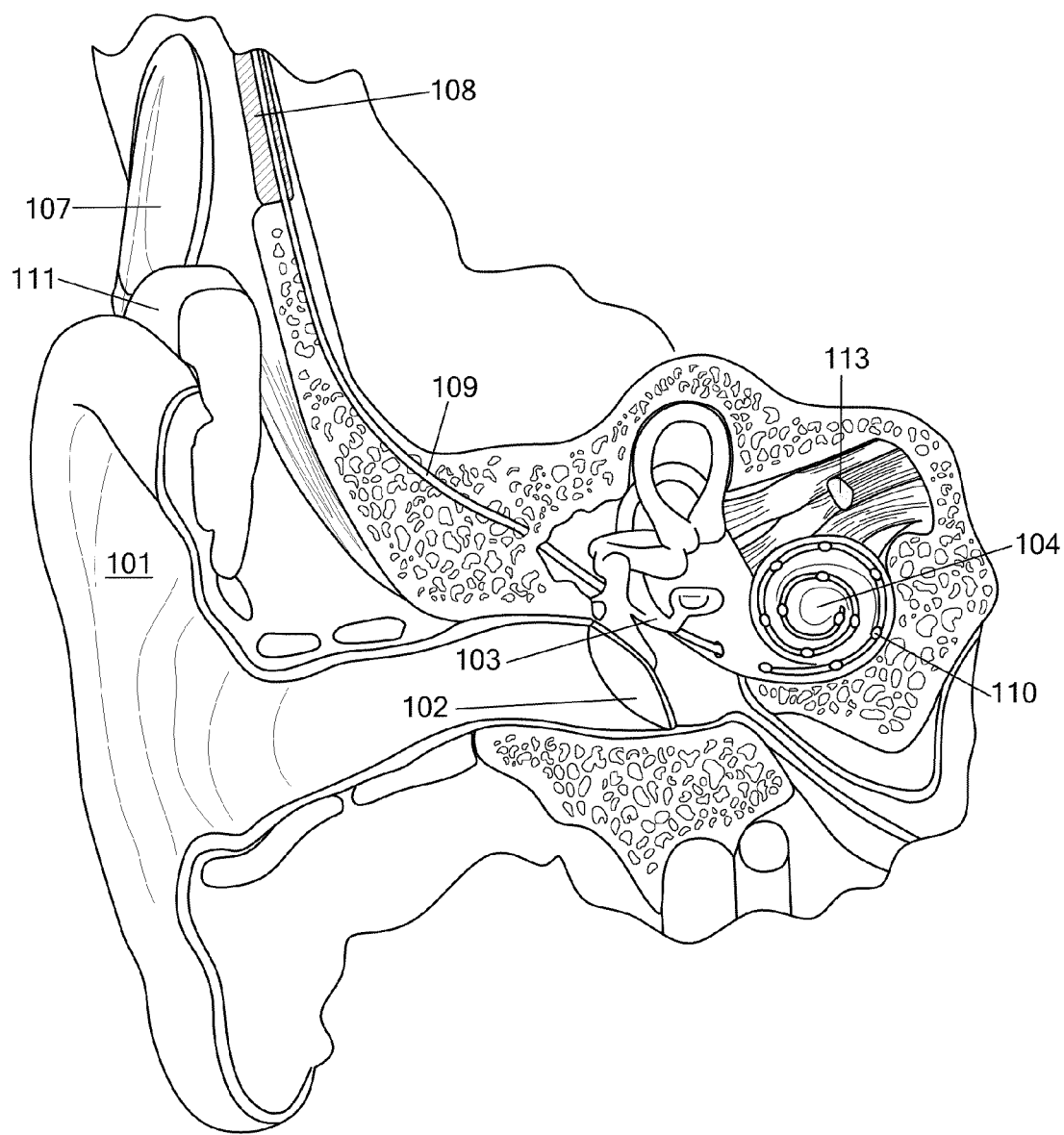
FIG. 1 shows elements of a human ear having a typical cochlear implant system.
Figure 2A:
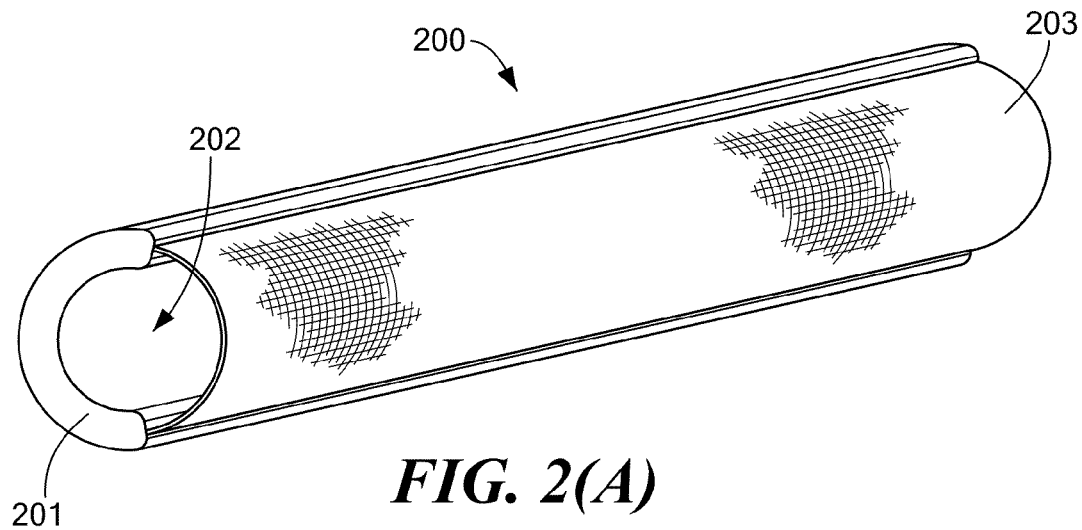
FIG. 2 shows perspective and cross-section views of an embodiment of an electrode shell.
Figure 2B:
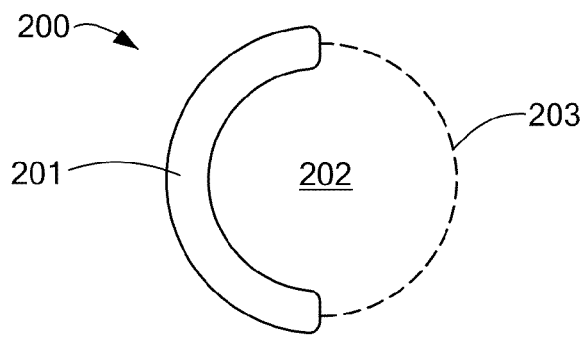

FIG. 2A shows a perspective view and FIG. 2B shows a cross-section of one specific example of an electrode shell 200 that protects the cochlear tissue from the direct friction and impact of the implant electrode. The electrode shell 200 is similar in shape and slightly larger than the implant electrode so that so that the implant electrode can easily slide in or out. A polymer insulator protector 201 provides the main structural support and encloses an interior volume 202 that covers some or all of the implant electrode. The insulator protector 201 also provides electrical isolation of other regions, at least in the close area around the implant electrode and its features. A conductive metal mesh grid 203 has openings that allow the electrode contacts on the implant electrode to electrically to deliver the electrical stimulation signals to the target audio nerve tissue by allowing current flow in the desired region with minimized current loss though the lateral cochlear wall. In other embodiments, the contact openings may be symmetrically disposed around the whole electrode shell 200, or only in specific locations, or only on one side of the electrode shell 200.

Embodiments of an electrode shell 200 act as a tissue protector that minimizes or suppresses much of the insertion trauma by cushioning to the implant electrode. Except for the initial insertion of the electrode shell 200, the affected tissues are protected from further damage. Embodiments of an electrode shell 200 may also allow the surface and external characteristics of the implant electrode to be more complex, non-smooth and non-uniform. This permits the development of new electrode designs free of the past constraints of smoothness, roundness, uniformity of surface. For example, an implant electrode may now be based on a thin film electrode with a very thin profile and sharp edges. In such an embodiment, the electrode shell 200 can absorb and deflect the sharp features of the electrode without damage to nearby tissues.

Once in place and deployed in its final fixed position (whether a scala tympani location or in the brain stem), the electrode shell 200 remains there and provides a directing conduit for insertion and removal of the implant electrode. During insertion of the implant electrode, the electrode shell 200 distributes the insertion pressure from the implant electrode against the electrode shell 200 instead of directly on the surrounding tissue. In this way, the force of the electrode insertion is distributed more generally and less trauma occurs.

The electrode shell 200 generally is implanted together with the implant electrode and it is intended to remain permanently fixed in the body, although an electrode shell 200 can also be designed for removable and retrieval from the body when necessary. The electrode shell 200 may be loaded together with the implant electrode that is inserted into the body tissue as a complete unit. Alternatively, the electrode shell 200 may be inserted into the tissue first, and then the implant electrode inserted into the electrode shell 200. The implant electrode can be easily removed from the electrode shell 200, which stays in place. The same or a new implant electrode can be re-loaded into the electrode shell 200 without causing additional damage to the surrounding tissue. If tissue or nerve growth has taken place since the initial insertion of the implant electrode into the electrode shell 200, then insertion or removal of the implant electrode from the electrode shell 200 causes very little additional disruption because the electrode shell 200 holds and protects the new growth.

It may also be useful to coat the electrode shell 200 with a therapeutic agent such as an antibiotic or a drug for promoting nerve regeneration and growth factor, or a tissue attachment promoter. Or such a therapeutic agent may be incorporated into some or all of the material of the electrode shell 200 to be released by elution of the therapeutic agent. In addition or alternatively, the electrode shell 200 may be coated in whole or in part with a lubricant to reduce insertion friction.

The electrode shell 200 may be pre-shaped to better fit into position. For example, the electrode shell 200 may be pre-curved to surround the modiolus. An embodiment of the electrode shell 200 may be relatively soft at room temperature and during insertion, and then harden and become more rigid with time, heat, hydration, or combination of these factors. Then after the electrode shell 200 becomes rigid, it provides a directional channel for insertion of the implant electrode. Alternatively or in addition, the electrode shell 200 may be folded for insertion into a small confined space, and then deployed after insertion by a releasing mechanism, for example, by mechanical, thermal, hydraulic, hydration, temperature, or shape memory action. In another embodiment, the electrode shell 200 may be an articulated structure that can easily bend along the length of a cavity such as the cochlea, and also take the upward spiraling structure of the cochlear channel.

One advantage of using an electrode shell 200 before insertion of the implant electrode is that the electrode shell 200 can be expressly designed to allow insertion in a given body cavity with minimal trauma because, unlike a prior art implant electrode, the electrode shell 200 is not burdened by the constrains imposed by the electrode wires and contacts and their encapsulator (silicone). Rather, the electrode shell 200 can be made of any biocompatible organic material such as a polymer or combination of metal and polymer. Another advantage is that the electrode shell 200 can be shaped, manipulated, and coated without fear of damaging or destroying key electrode components such as wires, contacts, encapsulator, etc.

The electrode shell 200 may be design to be fully inserted into the cochleostomy so that only a single opening is needed at the cochleostomy site. Or instead of insertion through the cochleostomy, an electrode shell 200 may be specially designed with an elbow shape for insertion through the round window and still guide the implant electrode to smoothly glide into the cochlea.

Figure 3:
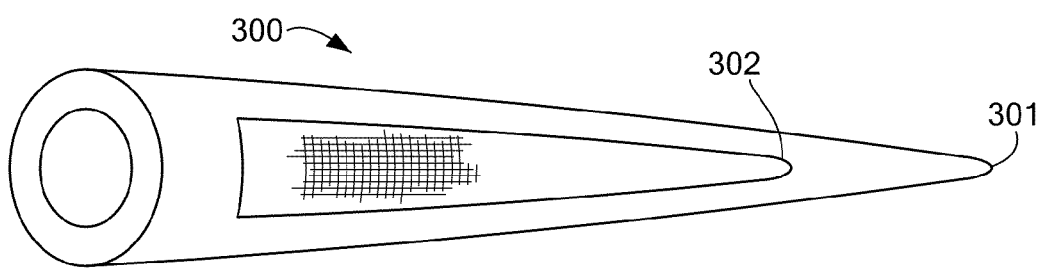
FIG. 3 shows an alternative funnel-shaped embodiment of an electrode shell.
Figure 4A:
FIG. 4 shows images of an electrode shell embedded in cochlear tissue.
Figure 4B:

FIG. 3 shows an example of a funnel-shaped electrode shell 300 wherein the exterior apical end 301 protects the surrounding tissue from the tip of the implant electrode. The electrode shell 300 is generally softer and easier to insert than a conventional implant electrode. The interior apical end 302 has a spherical section shape that can receive a ball end of a flexible rod insertion tool for pushing the electrode shell 300 into a desired location within the cochlea (See, e.g., electrode shell 400 in FIG. 4 A-B). The interior apical end 302 also forms an electrode capture connection for capturing the end of the implant electrode within the electrode shell 300 when insertion is complete, and similarly an electrode release connection for releasing the implant electrode from the electrode shell 300 retracting the implant electrode if later removal of the electrode is required.

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant device comprising:
   an electrode shell for insertion into a fixed position in cochlear tissue, the electrode shell including:
   i. an interior volume completely surrounding a portion of an implant electrode having an outer surface with a plurality of electrode contacts, and
   ii. an outer surface including:
      (a) an electrically insulating portion made of polymer insulator material and configured to fit over the implant electrode without covering the electrode contacts to provide electrical isolation of the electrode contacts from the cochlear tissue around the electrically insulating portion of the electrode shell, and
      (b) an electrically conductive portion made of a metallic mesh and configured to fit over the implant electrode so that the electrode contacts are exposed for delivering electrical stimulation signals to the cochlear tissue adjacent to the electrically conductive portion.

2. A device according to claim 1, wherein the electrode shell includes an electrode release connection for releasing the implant electrode from the electrode shell for retracting the implant electrode with minimal trauma to the cochlear tissue.

3. A device according to claim 1, wherein the electrode shell includes an electrode capture connection for capturing the implant electrode within the electrode shell for inserting the implant electrode with minimal trauma to the cochlear tissue.

4. A device according to claim 1, wherein the electrode shell includes a therapeutic substance for release into the cochlear tissue.

5. A device according to claim 4, wherein the therapeutic substance is a coating on the outer surface of the electrode shell.

6. A device according to claim 4, wherein the therapeutic substance is integrated into the polymer insulator material of the electrode shell.

7. A device according to claim 1, further comprising:
   a lubricant coating on the outer surface of the electrode shell to reduce friction for insertion in the cochlear tissue.

8. A device according to claim 1, wherein the electrode shell is pre-curved for proper fit in the fixed position.

9. A device according to claim 1, wherein the electrode shell is adapted to initially be flexible for insertion into the fixed position, and then to harden to become rigid after insertion into the fixed position.

10. A cochlear implant electrode covered by an electrode shell according to any of claims 1-7, 8 and 9.

* * * * *